United States Patent [19]

Kawaguchi

[11] Patent Number: 5,166,234
[45] Date of Patent: Nov. 24, 1992

[54] BISUREA LIGHT STABILIZER FOR ORGANIC POLYMERS

[75] Inventor: Akitsugu Kawaguchi, Waynesboro, Va.

[73] Assignee: E. I. Du Pont de Nemours and Company, Wilmington, Del.

[21] Appl. No.: 620,253

[22] Filed: Nov. 30, 1990

Related U.S. Application Data

[60] Division of Ser. No. 347,905, May 5, 1989, Pat. No. 5,081,258, which is a continuation-in-part of Ser. No. 196,591, May 19, 1988, abandoned.

[51] Int. Cl.$^5$ ............................................... C08K 5/34
[52] U.S. Cl. ..................................................... 524/91
[58] Field of Search ........................................ 524/91

[56] References Cited

U.S. PATENT DOCUMENTS

| | | | |
|---|---|---|---|
| 4,853,471 | 8/1989 | Rody et al. | 524/91 |
| 4,894,400 | 1/1990 | Haruna et al. | 524/91 |
| 5,032,498 | 7/1991 | Rody et al. | 524/91 |

Primary Examiner—Kriellion S. Morgan

[57] ABSTRACT

A hydroxyphenyl-benzotriazole bisurea UV light stabilizer for organic polymers and a process for making it are provided. The stabilizer is particularly useful for spandex polymer yarns that are subjected to solvent scouring. A preferred stabilizer of the invention is a bisurea formed by reacting methylene-bis(4-phenylisocyanate) with 2-[2-hydroxy-3-(1,1-dimethylethyl)-5-(N-aminoethyl)propionamid-phenyl ]-2H-benzotriazole.

3 Claims, No Drawings

BISUREA LIGHT STABILIZER FOR ORGANIC POLYMERS

RELATED APPLICATION

This is a division of application Ser. No. 07/347,905, filed May 5, 1989, now U.S. Pat. No. 5,081,258, issued Jan. 14, 1992, which in turn was a continuation-in-part of application Ser. No. 07/196,591, filed May 19, 1988, now abandoned.

BACKGROUND OF THE INVENTION

1. Field of the Invention

This invention relates to chemical compounds which are used as stabilizers for protecting polymers against degradation that is induced by exposure to ultraviolet light. Specifically, the invention concerns such a UV-stabilizer, which is a bisurea compound that includes two 2-(2'-hydroxyphenyl)benzotriazole groups.

2. Description of the Prior Art

Many compounds are known in the art for use as UV-stabilizers for organic polymers. Among the known UV-stabilizers are 2-(2,-hydroxyphenyl)benzotriazoles of the type disclosed by Canadian Patent 1,197,246 to Ciba-Geigy AG. Ciba-Geigy sells such UV-stabilizers under the "Tinuvin" trade names. These include, for example, "Tinuvin" 213, also referred to as "Tinuvin" 1130, which is mainly the 2-[2-(2-hydroxy-ethoxy)ethoxy]ethylester of 3-(2H-benzotriazol-2-yl)-4-hydroxy-5-(1,1-dimethylethyl)-benzene propanoic acid).

Although the 2-(2,-hydroxyphenyl)benzotriazoles have been useful in many organic polymers, when used as UV-stabilizing additives in spandex fibers certain shortcomings are evident. For example, spandex fibers often are converted into fabrics or garments that are subjected to solvent scouring and various dry-cleaning solvents. Solvents, such as perchloroethylene and other non-polar solvents, are used extensively. However, such solvents extract the hydroxy-benzotriazole additives from the polymeric fibers, thereby reducing the UV-protection for the fibers. Also, some of the known hydroxyphenyl-benzotriazole UV-light stabilizers have caused accelerated degradation of spandex in the presence of aqueous hypochlorite solutions. Such solutions are commonly used as laundry bleaches. Furthermore, some known hydroxyphenyl-benzotriazole stabilizers have a tendency to form colored complexes when exposed to copper ions. In spandex, these stabilizers can cause yellow discoloration during textile finishing or in laundering, if the water used contains copper ions (e.g., as might be present in water supplied through copper pipes).

It is a purpose of this invention to overcome, or at least significantly reduce, the above-recited shortcomings of the known hydroxyphenyl-benzotriazole UV-stabilizers and to provide a UV-stabilizer that is not readily extracted from polymer by scouring and dry-cleaning solvents, is relatively unaffected by common laundry bleaches and is not detrimentally affected by the presence of copper ions.

Although not related to 2-(2'-hydroxyphenyl)benzotriazole UV-light stabilizers, bisurea compounds per se, as well as for other types of stabilizers, are known in the art, as for example from Japanese Patent 46/13143 to Teijin Ltd.

SUMMARY OF THE INVENTION

The present invention provides an ultraviolet-light stabilizer for organic polymers, the stabilizer being a bisurea compound of the structural formula (I)

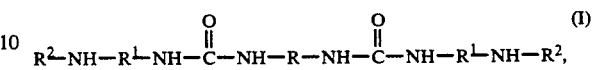

wherein
R denotes a divalent group which connects the two isocyanate groups of an organic diisocyanate, preferably bis(p-phenylene)methane, bis(4-cyclohexylene)methane or 3,3,5-trimethyl-5-methylenecyclohexyl,
$R^1$ is a saturated hydrocarbon chain of 2 or 3 carbon atoms and
$R^2$ denotes a monovalent radical containing a 2-(2'-hydroxyphenyl)benzotriazole group, preferably, 3-(2H-benzotriazol-2-yl)-4-hydroxy-5-(1,1-dimethylethyl)benzenepropanoyl. A particularly preferred UV-stabilizer of the invention has the structural formula (II)

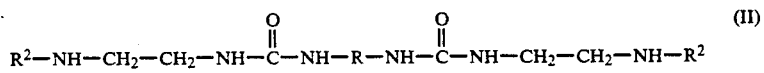

where R is bis(p-phenylene)methane and $R^2$ is 3-(2H-benzotriazol-2-yl)-4-hydroxy-5-(1,1-dimethylethyl)-benzenepropanoyl.

The present invention also provides (a) a process for preparing the UV-light stabilizer, (b) a new compound that is useful as an intermediate for preparing the UV-stabilizer, (c) a polymer containing an effective amount of the stabilizer and (d) a spandex yarn containing the stabilizer.

DETAILED DESCRIPTION OF PREFERRED EMBODIMENTS

The 2-(2'-hydroxyphenyl)benzotriazole bisurea compounds of the invention are suitable for use as UV-light stabilizers for organic polymers, including polyolefins, polyurethanes, polyamides, polyaramides, elastomeric polyurethanes, and the like. The compounds of the invention are believed to be effective UV-light stabilizers for any polymer in which current commercial 2-(2'-hydroxyphenyl)benzotriazole UV-light stabilizers have been used satisfactorily. However, the bisurea compounds of the invention are most useful in segmented elastomers, especially spandex polymers which have polyether soft segments.

In the 2-(2'-hydroxyphenyl)benzotriazole bisurea UV-stabilizers of the invention, the hydroxyl group is located on the phenyl ring in the ortho position with respect to the benzotriazole group. In addition, the phenyl group optionally can have other substituents, such as linear or branched alkyl or arylalkyl groups. The benzotriazole group may also contain substituents such as halogen or alkyl groups. Such substituents are believed to protect the phenolic group, to prevent harmful substitutions in the ortho or para positions, or to modify the UV-absorption spectrum of the stabilizer. In addition, branched alkyl groups with no more than eight carbon atoms or α-substituted benzyl groups in the ortho position to the phenolic hydroxyl group are believed to increase the effectiveness of hydroxyphenyl-benzotriazole stabilizers by affecting the steric position of the hydroxyl group versus the triazole ring atoms. The UV protection provided by the hydroxyphenyl-benzotriazole light stabilizers is believed to be due to their screening action, which results from their strong absorption of ultraviolet light.

To function effectively as a UV-light stabilizer in an organic polymer, the stabilizer of the invention usually is present in a concentration of at least 0.1%, and seldom greater than 5%, based on the weight of the polymer. For spandex polymer, the preferred concentration range is 0.5% to 1.5%. In general, spandex compositions with polyether soft segments need somewhat higher stabilizer concentrations than those with polyester soft segments. In other polymers, a different optimum concentration range may apply.

The effectiveness of the UV-light stabilizers of the invention can be enhanced by adding other stabilizers, such as phenolic antioxidants, hindered amines and/or phosphites, to the polymer. Additives, that are radical scavengers are especially beneficial. Such radical scavengers (e.g., phenolic antioxidants) prevent degradation which can result from radical chain reactions which may have been initiated in spite of the presence of the hydroxyphenyl-benzotriazole.

The UV-stabilizers of the invention can be incorporated into polymers by conventional techniques, much in the same way as other stabilizers are incorporated. For solution-spun spandex, the preferred way is to mix the stabilizer with other additives and a dilute polymer solution to form a slurry which can be mixed with polymer solution for spinning, as described in Example 2, below. The compounds of the invention are soluble in commonly used spandex-spinning solvents, such as dimethylformamide and dimethylacetamide, which facilitates their incorporation into the spinning solutions and avoids formation of particles which may plug the spinnerets.

The process of the present invention comprises forming a 2-(2'-hydroxyphenyl)benzotriazole derivative (referred to herein as an intermediate product) that has a substituent which includes a group capable of reacting with an organic diisocyanate, and then reacting the intermediate product with an organic diisocyanate to form the desired 2-(2'-hydroxyphenyl)benzotriazole bisurea UV-stabilizer of the invention. Preferably, the diisocyanate is selected from the group consisting of p,p'-methylene diphenyl diisocyanate, 4,4,-methylene-bis(cyclohexylisocyanate) and isophorone diisocyanate. In a preferred process, the methyl ester of 3-(2H-benzotriazole-2-yl)4-hydroxy-5-(1,1-dimethyl ethyl)benzenepropanoic acid is reacted with excess ethylene diamine to form 2-[3-(2H-benzotriazole-2-yl)-4-hydroxy-5-(1,1-dimethylethyl)-benzene propanoyl]amido-ethylamine, which is then reacted with MDI to form a hydroxyphenyl-benzotriazole bisurea UV-stabilizer of the invention. Instead of the methyl ester of 3-(2H-benzotriazole-2-yl)-4-hydroxy-5-(1,1-dimethylethyl)benzenepropanoic acid, other esters of this acid can be employed as the starting material.

Commercially available 2-(2'-hydroxyphenyl)benzotriazole light stabilizers sometimes contain ester groups. Such benzotriazoles (e.g., "Tinuvin" 213) are particularly suited for preparation of bisureas according to the invention. The ester derivatives of benzotriazoles can be synthesized by known methods of organic chemistry and then converted into amide-amines by reaction with excess of a diamine to yield intermediates suitable for preparation of bisurea stabilizers according to the invention. However, it is not necessary to start with esters, or to use amide-amine derivatives, to synthesize compounds of the above general structural formula.

Other starting materials useful for preparing bisurea stabilizers of the invention include 2-(2'-hydroxy-3-chloracetamidomethyl-5-methyl-phenyl)-2H-benzotriazole and 3-[3-(2H-benzotriazol-2-yl)-4-hydroxy-5-(1,1-dimethylethyl)-phenyl]-propyl chloride. A Gabriel reaction, for example, can be used to convert these starting materials into an intermediate which contains an amine group that is capable of reacting with diisocyanates to form the desired 2-(2,hydroxyphenyl)benzotriazole UV-light stabilizer.

In the above-described processes, the intermediate that is formed has the following generalized structural formula (III):

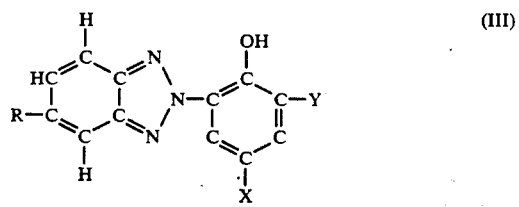

where R is lower alkyl or halogen, either the X or Y group is -R'-NH2 in which R' is a linking moiety optionally containing amide linkages, and the other X or Y group is substituted or unsubstituted alkyl or aralkyl. These intermediates are most convenient for conversion into the bisureas of the invention by reactions with the preferred organic diisocyanates, methylene-bis(4-phenylisocyanate), 4,4,-methylenebis(cyclohexylisocyanate) or isophorone diisocyanate.

In the Examples which follow, several tests are employed to the determine the effectiveness of UV-light stabilizers in preventing degradation and discoloration of yarns of spandex polymer.

Accelerated UV-light exposure tests are performed in an Atlas Weatherometer. In these tests, spandex fibers are exposed while stretched, to accelerate any degradation. Degradation is more rapid because of the smaller diameter of the stretched fiber and the fibers exhibit irreversible "growth" in the early stages of degradation. In each test, a set of ten spandex threads, held just taut (i.e., straight), is clamped in a metal rack with 10 cm between the clamps. The clamps are then moved apart to a distance of 15 cm, stretching the threads 50%. The stretched threads are then exposed for 20-hour periods in the weatherometer. After each exposure period, the samples are relaxed for 15 minutes by moving the clamps together until the strands are slack. The final length of the threads, L, is then measured with the threads held just taut enough to straighten the threads. The growth of the thread is expressed as a percent of amount of stretch in the thread while under test and is calculated by the formula $$\% \text{ growth} = (100)(L-10)/(15-10) = 20(L-10).$$

Discoloration from UV-exposure, usually yellowing, is measured by an increase in "b" value with a "Colorquest" colorimeter sold by Hunter Laboratories. Yarns are wound on cards until the card is well covered. The yarn-covered cards are then subjected to light-exposure testing. The "b" values of the samples are recorded before and after exposure. The change in "b" value is a measure of the amount of yellowing.

The resistance of a UV-stabilizer to extraction from a polymeric substrate by conventional scouring and dry-cleaning solvents is measured by one of two tests; one for film samples and one for fiber samples.

For polymeric films, a 5-gram sample of film containing a light stabilizer is immersed for 2 minutes in 0.1 liter of perchloroethylene solvent which is stirred and maintained at 45° C. After removal from the solvent and drying, the film is weighed. The weight loss of the film sample is compared to the weight loss of a control sample that was exposed to the same extraction treatment. The control sample is of the same composition as the test sample but does not contain any UV-stabilizer. The difference in percent weight loss between the test sample and the control sample represents the weight loss of UV stabilizer by the test sample and is expressed as a percentage of the original amount of UV-stabilizer. The latter percentage is reported as the "% extractability" of the UV-stabilizer.

For samples of polymeric fibers which contain several different additives, the following test is used. A 20-gram sample of yarn is cut into pieces and then immersed and stirred for two minutes in 200 milliliters of perchloroethylene maintained at 45° C. The fibers are then filtered from the liquid. The perohloroethylene filtrate is vacuum evaporated to leave a first residue which includes any additives or finishes that were removed from the sample by the perchloroethylene, along with any of the UV-stabilizer that was removed. To facilitate analysis of the individual components of the residue, the residue is separated into two fractions by extraction with hexane, a hexane-insoluble fraction and a hexane-soluble fraction. Evaporation of the hexane then results in a hexane-insoluble "Residue A" and a hexane-soluble "Residue B". Residues A and B are then analyzed by NMR (nuclear magnetic resonance) in deuterated chloroform to determine the amount of stabilizer in each of Residues A and B. The percent extractability of the UV-stabilizer is then calculated as 100 times the total amount of stabilizer in the combined residues divided by the amount present initially in the 20-gram yarn sample.

To measure the bleach-resistance of a spandex fiber, weighted samples of fiber strands are suspended in an aqueous bath. The bath is maintained at a pH of 7, a temperature of 28° C. and an active chlorine concentration of 500 ppm. In the tests reported in Example I, a 5.8-gram weight is hung from a loop of 44-dtex spandex strand and the weighted strand is placed in the bath. The exposure is continued until the strand breaks. The duration of the test exposure is recorded. A UV-stabilizer that does not accelerate chlorine-induced degradation, usually permits spandex strands to endure for several hours in this test.

To determine the sensitivity of a spandex yarn containing a specific additive to discoloration in the presence of copper ions, the following test is used. To 1 liter of water, 268.3 milligrams of copper chloride dihydrate are added to give a solution containing 10 ppm of copper. A 1-gram sample of the yarn is soaked for four hours in 60 milliliters of the solution maintained at 45° C. The yarn is then removed from the solution, washed with tap water and dried. The yellowness of the yarn sample is compared by eye to the yellowness of yarns containing other stabilizers that were exposed to the same test conditions.

The examples which follow illustrate preferred embodiments of the invention, but are not intended to limit its scope, which is defined by the claims below. The following abbreviations and tradenames are used:

| | |
|---|---|
| MDI | methylene-bis(4-phenylisocyanate). |
| PICM | 4,4'-methylene-bis(cyclohexylisocyanate). |
| IPDI | isophorone diisocyanate. |
| TDI | tolylene diisocyanate. |
| DMAc | N,N-dimethylacetamide. |
| Tinuvin 213 | the 2-[2-(2-hydroxy-ethoxy)-ethoxy]ethyl-ester of 3-(2H-benzotriazol-2-yl)-4-hydroxy-5-(1,1-dimethylethyl)-benzene propanoic acid), sold by Ciba-Geigy. |
| Cyanox 1790 | 1,3,5-tris(4-t-butyl-3-hydroxy-2,6-dimethylbenzyl)-1,3,5-triazine-2,4,6-(1H,3H,5H)trione, an antioxidant sold by American Cyanamid. |
| DIPAM/DM | a copolymer of diisopropylaminoethyl methacrylate and n-decyl methacrylate in a 75:25 weight ratio, a dye enhancer. |
| Tone 2000 | a poly(caprolactone) diol of 2000 number average molecular weight, sold by Union Carbide. |
| Duponol EP | a detergent sold by E. I. du Pont de Nemours & Co. |

Also, as used herein, the term "spandex" has its usual definition; that is, a long chain synthetic polymer that comprises at least 85% by weight segmented polyurethane.

EXAMPLE I

This example illustrates the preparation of a preferred 2-(2'-hydroxyphenyl)benzotriazole bisurea UV-stabilizer compound of the invention and its advantageous use in a spandex polymer yarn. The performance of the yarn is compared to spandex polymer yarns of the same composition but which (1) contain as UV-stabilizer, the 2-(2'-hydroxyphenyl)-benzotriazole from which the preferred bisurea compound of the invention was prepared (Comparison Yarn A) and (2) contain no UV-stabilizer (Comparison Yarn B).

A solution of a hydroxyphenyl-benzotriazole bisurea stabilizer was prepared by dissolving 454 grams of "Tinuvin" 213 UV-stabilizer in 4 liters of methanol; adding 5 grams of p-toluenesulfonic acid; and heating the solution for 72 hours under reflux. The solution was then cooled to room temperature. A solid preciptate formed, which was separated from the liquid by filtration and then dried to form a yellowish powder that weighed 246 grams. The powder was the methyl ester of 3-(benzotriazol-2-yl)-4-hydroxy-5-t-butyl-benzene-propanoic acid. A 210-gram portion of the methyl ester was dissolved in 1,800 grams of ethylene diamine and heated under reflux for 18 hours. Excess ethylene diamine and evolved methanol were removed by vacuum evaporation. An orange residue remained. The residue was added to and stirred with 3 liters of di-isopropyl ether. An amide-amine intermediate product was precipitated which after filtration and drying, had a slightly yellow color and weighed 174 grams. The residue was dissolved in toluene and recrystallized. The recrystallized residue, which melted at 146° C., was 2-[2-hydroxy-3-(1,1-dimethylethyl)-5-(N-aminoethyl)pro-pionamid-phenyl]-2H-benzotriazole. This chemical is of the structure given by Formula III above, in which

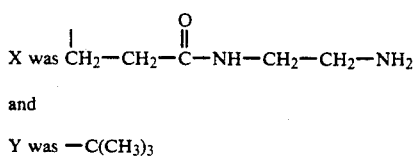

and

Y was —C(CH₃)₃

To a stirred solution of 128.8 grams of the thusly-obtained amide-amine intermediate product in 800 ml of DMAc, a solution of 42.3 grams of MDI in 200 ml of DMAc was added. During the addition, the reaction mixture was cooled in ice to maintain the temperature below 40° C. The resulting solution contained a bisurea compound of the invention having the following structural formula:

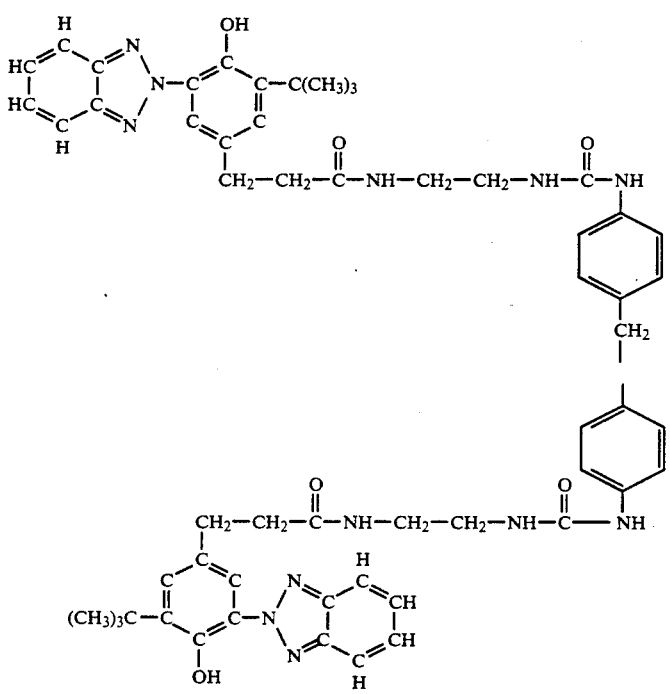

A spandex yarn was prepared and stabilized with the hydroxyphenyl-benzotriazole bisurea UV-stabilizer described in the preceding paragraph as follows. A solution was prepared of a segmented polyether-based polyurethane spandex polymer in DMAc by the general procedure described in U.S. Pat. No. 4,340,527, Example I. "Cyanox" 1790 antioxidant, DIPAM/DM dye enhancer, Tone 2000 polyol and bisurea UV-stabilizer of the preceding paragraph were added to the solution in quantities that provided to the final spandex fibers additive concentrations of 1.5%, 2.0%. 0.5% and 1.0%, respectively, based on the final weight of the fiber (without finish).

The above-described spandex polymer solution was dry-spun in a conventional manner through orifices to form coalesced 4-filament, 44-dtex yarns. Comparison Yarns "A" and "B" were spun from the same solution, except that for Yarn A, "Tinuvin" 213 was substituted for the UV-stabilizer of the invention, and for Yarn B, no UV-light stabilizer was included.

The above-described yarns were tested for growth on exposure to UV-light, extractability of the UV stabilizer by solvent and discoloration by copper ions. The results of the tests are summarized in the following table.

TABLE I

| Yarn Sample | Of Invention | Comparison A | Comparison B |
|---|---|---|---|
| Stabilizer | Example I* | Tinuvin 213 | None |
| Weight % | 1.0 | 1.0 | 0 |
| UV-exposure 20-hr growth, % | 17.5 | 21.3 | 30.8 |
| Extractability, % extracted | 12 | 45 | — |
| Copper ion test final color | light yellow | yellow | clear |

*As described in the the second paragraph of Ex. I.

The UV-growth data summarized in the table show that the UV-stabilization provided by the bisurea compound of the invention is at least as good as, if not somewhat better than, that provided by Tinuvin 213, at approximately the same concentration of hydroxyphenyl-benzotriazole. After being subjected to solvent scouring and a subsequent 20-hour Weatherometer exposure test, the sample yarn containing the bisurea compound of the invention still exhibited a growth of only 23.1%. In contrast, the Comparison Yarn A, which contained "Tinuvin" 312, exhibited a 32.8% growth and the Coparison Yarn B, which contained no UV-stabilizer at all, broke in testing.

The three yarns were also tested for degradation by chlorine laundry bleach. Average break times for the Comparison Yarn B (no UV-stabilizer) was 109 minutes. Comparison Yarn A (containing 1% "Tinuvin" 213) exhibited a break time of 52 minutes, indicating that this commercial UV-stabilizer accelerated chlorine-induced degradation. The yarn containing the bisurea UV-stabilizer of the invention broke after 100 minutes. Thus, in contrast to the commercial stabilizer, the bisurea UV-light stabilizer of the invention had only a very a small effect, if any, on chlorine-induced degradation of the spandex fibers.

EXAMPLE II

Yarns were prepared as in Example I, except that 3.0% zinc oxide, based on finish-free fiber weight, was added to the spinning solutions in the form of a slurry, substantially by the same procedures as described in U.S. Pat. No. 4,340,527. The yarns were wound on thin, rectangular metal plates and then subjected to a simulated finishing treatment. In the treatment, the samples of wound yarn were immersed for 60 minutes in water containing 0.3 gram per liter of ethylenediamine tetraacetic acid and 1.5 gram per liter each of tetrasodium pyrophosphate and "Duponol EP". The wound yarn samples were then exposed for 40 hours to UV-light in the Weatherometer. The following increases in "b" values were observed to have resulted from the combined finishing and light-exposure treatments:

TABLE II

| Yarn Sample | Of Invention | Comparison A | Comparison B |
|---|---|---|---|
| Stabilizer | Example I* | Tinuvin 213 | None |
| Weight % | 1.0 | 1.0 | 0 |
| Increase in "b" value | 8.1 | 8.4 | 11.3 |

*See Example I, Table I.

The data recorded in Table II again show that with regard to protection against UV-light-induced discoloration, the 2-(2'-hydroxyphenyl)benzotriazole bisurea UV-stabilizer of the invention is as good as, if not somewhat better than, the commercial 2-(2'-hydroxyphenyl)-benzotriazole (i.e., "Tinuvin"-213) from which the stabilizer of the invention was made. However, as shown in Example I, the bisurea stabilizer compounds of the invention are considerably better in resistance to copper-ion-induced discoloration, chlorine-induced degradation and extractability of the stabilizer by scouring and/or dry-cleaning solvents.

Advantageous results, similar to those reported above, are obtained when this example is repeated with the R in Formula I being provided by PICM or IPDI, instead of by MDI as in this example and in Example I.

EXAMPLE III

This example illustrates the advantageous low extractability of various bisurea UV stabilizers of the invention made with R groups (of Formula I) derived from different organic diisocyanates.

The procedure of Example I for preparing solutions of spandex polymer was repeated except that the antioxidant, the dye enhancer and the polyol additives were omitted. UV stabilizers were added to the polymer solutions to form the following samples. Unless noted otherwise, the concentration of UV stabilizer was 1.0% based on the weight of polymer in solution:

| Sample III-1 | bisurea UV stabilizer prepared as in Example I. |
|---|---|
| Sample III-2 | bisurea prepared as in Ex. I, except the MDI was replaced by 44.3 grams of PICM. |
| Sample III-3 | bisurea prepared as in Ex. I, except the MDI was replaced by 37.6 grams of IPDI. |
| Sample III-4 | bisurea prepared as in Ex. I, except the MDI was replaced by 29.4 grams of TDI. |
| Comparison C | "Tinuvin" 213. |
| Comparison D | no UV-light stabilizer added. |

Films were cast from the above-described solutions onto "Mylar" polyester sheets. A doctor knife with a 0.25-mm clearance was used. The cast film was placed in an oven heated to 70° C. for about 16 hours to permit the solvent to evaporate from the film. The films were then exposed in perchloroethylene in accordance with the extractability test described hereinbefore. The following table summarizes the results of the test:

TABLE III

| | % Extractability |
|---|---|
| Sample of Invention | |
| III-1 | 10 |
| III-2 | 10 |
| III-3 | <5 |
| III-4 | 10 |
| Comparison Sample | |
| C | 80 |
| D | — |

The data of Table III on the extractability of UV stabilizer by solvents, such as perchloroethylene, clearly show the vast superiority of the bisurea stabilizers of the invention over the known commercial stabilizer (Comparison C) from which the bisureas of samples III-1 through III-4 of the invention were derived. In these tests, 80% of the commercial UV stabilizer ("Tinuvin" of Comparison Sample C) was extracted from the film by the perchloroethylene. In contrast, 10% or less of the bisurea UV stabilizers of the invention was extracted by the solvent.

I claim:

1. A fiber formed from an organic polymer having dispersed therein an ultraviolet-light stabilizer in a concentration range of 0.1 to 5 percent based on the weight of the polymer, the stabilizer being a bisurea compound of the structural formula (I)

wherein
R denotes a divalent group which remains after removal of the two isocyanate groups of an organic diisocyanate and is selected from the group consisting of bis(p-phenylene)methane, bis(4-cyclohexylene)methane, 3,3,5-trimethyl-5-methylenecyclohexyl and tolylene,
$R^1$ is a saturated hydrocarbon chain of 2 or 3 carbon atoms and
$R^2$ denotes 3-(2H-benzotriazol-2-yl)-4-hydroxy-5-(1,1-dimethylethyl)benzenepropanoyl.

2. A fiber in accordance with claim 1 wherein the fiber is formed from a spandex polymer and the concentration range is 0.5 to 1.5 percent based on the weight of the polymer.

3. A fiber in accordance with claim 2 wherein R is bis(p-phenylene)methane and $R^1$ is —$CH_2$—$CH_2$—.

* * * * *